US005623942A

United States Patent [19]
Pestes et al.

[11] Patent Number: 5,623,942
[45] Date of Patent: Apr. 29, 1997

[54] CELL COLLECTION SWAB

[75] Inventors: Cornelius N. Pestes; Larry L. Pestes, both of Boring, Oreg.

[73] Assignee: MML Diagnostics, Troutdale, Oreg.

[21] Appl. No.: 590,531

[22] Filed: Jan. 24, 1996

[51] Int. Cl.⁶ .................................................. A61B 10/00
[52] U.S. Cl. .................................................. 128/759; 128/749
[58] Field of Search .................................. 128/749–758, 128/759

[56] References Cited

U.S. PATENT DOCUMENTS

| | | | |
|---|---|---|---|
| 2,839,049 | 6/1958 | MacLean | 128/756 |
| 4,952,204 | 8/1990 | Korteweg | 128/759 |
| 4,981,143 | 1/1991 | Sakita et al. | 128/757 |
| 5,022,408 | 6/1991 | Mohajer | 128/756 |
| 5,031,635 | 7/1991 | Koll | 128/759 |
| 5,084,005 | 1/1992 | Kachigian | 128/756 |
| 5,096,062 | 3/1992 | Burkardt et al. | 128/759 |
| 5,121,752 | 6/1992 | Canna | 128/759 |
| 5,425,377 | 6/1995 | Caillouette | 128/759 |
| 5,522,795 | 6/1996 | Green et al. | 128/759 |

*Primary Examiner*—Sam Rimell
*Assistant Examiner*—Pamela Wingood
*Attorney, Agent, or Firm*—Chernoff, Vilhauer, McClung & Stenzel

[57] ABSTRACT

A swab for collecting cell samples from a male urethra including a unitary elongate shaft having a constant diameter cylindrical handle at one end and a tapered circular cross-sectioned probe at the other end. The shaft is injection molded from a glass filled nylon material with the fiberglass being between 5 and 20 percent by volume and preferably being 10 percent by volume. A fiber tip is mounted at the end of the probe to collect cell specimens.

7 Claims, 1 Drawing Sheet

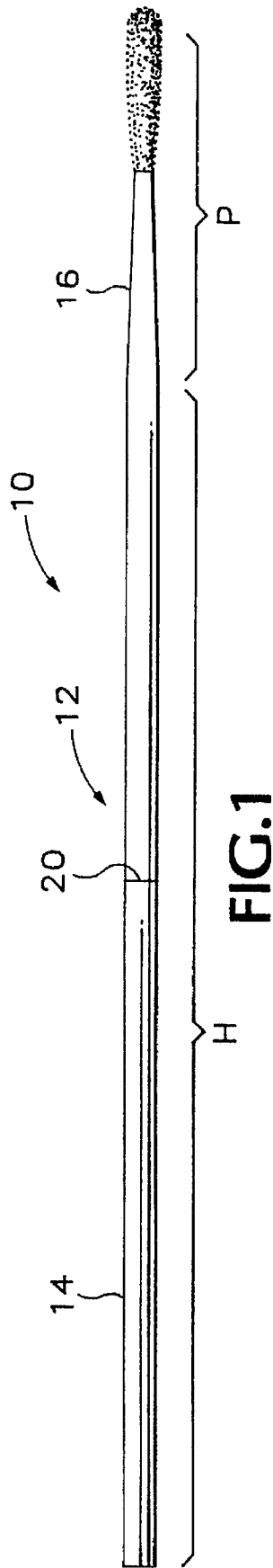
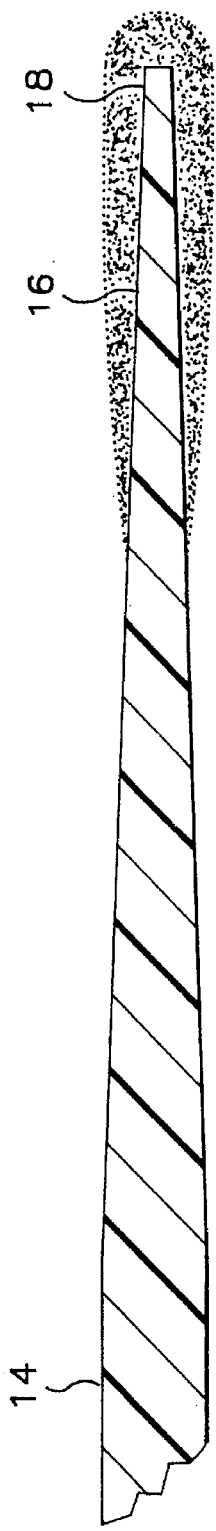
FIG.1
FIG.2 PRIOR ART
FIG.3

5,623,942

CELL COLLECTION SWAB

BACKGROUND AND SUMMARY OF THE INVENTION

This invention relates to a swab for collecting cell samples, and in particular to such a swab for use in collecting samples from the male urethra.

In order to diagnose certain urinary tract or genital diseases or to perform certain types of DNA testing, it is necessary to collect cell samples from the patient's urethra. This process has inherent difficulties with respect to males due to the small size of the urethra and the sensitivity surrounding its opening. First of all the probe end of the swab shaft must be small enough that when covered with the fiber tip that is used to capture cells it will fit comfortably in the urethra. At the same time the handle at the other end of the swab shaft must be sufficiently large to allow it to be firmly gripped. In addition, the swab shaft must be ductile enough so that it will not break and yet be stiff enough that it will not flex excessively during use.

This has been accomplished in the past with a two piece swab shaft. A hollow cylindrical handle has a smaller diameter stainless steel probe inserted into one end. The probe is heat-sealed to the handle. A fiber tip is then attached to the end of the probe. In order to prevent contamination of the collected cells during transportation to the laboratory, a swab of this type is partially inserted into a specimen tube and the protruding portion of the handle is broken off. The handle is scored to provide for breakage at the desired point. In the past this has been accomplished by rotating the handle under a blade.

Because of the cost of the stainless steel probe and the amount of hand assembly work, the prior art swabs are relatively expensive. In addition, carbon in the stainless steel probe may affect the results of DNA testing of samples collected with the swab.

The subject invention overcomes the foregoing problems associated with the prior art swabs by providing a unitary elongate glass filled nylon shaft which has a constant diameter circular cross-sectioned handle at one end and a tapered circular cross-sectioned probe at the other end. The shaft is between 5 and 20 percent fiberglass by volume and preferably is 10 percent fiberglass by volume. A fiber tip is located at the end of the probe to collect cell samples.

Preferably the probe covers approximately 25 percent of the overall length of the shaft and the diameter of the end of the probe is approximately one-third of the diameter of the handle. In the preferred embodiment, the handle has a diameter of approximately 0.100 inches and the end of the probe has a diameter of approximately 0.035 inches. The probe is made by injection molding and a score line is formed in the handle approximately at the midpoint of the shaft, as part of the molding process.

As a result of its shape and material, the subject swab provides similar size, strength and stiffness characteristics as the prior art two piece swabs at far less cost and with an inert probe.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 1 is a side elevation view of a swab embodying the subject invention.

FIG. 2 is a side elevation view of a prior art swab.

FIG. 3 is a detail view of the probe end of the swab of FIG. 1 in cross-section and at an enlarged scale.

DETAILED DESCRIPTION OF THE PREFERRED EMBODIMENT

Referring to FIG. 1 of the drawings, a swab 10 for collecting cell samples from a male urethra comprises an elongate unitary shaft 12. The shaft preferably is circular in cross-section and includes a constant diameter handle 14, designated as "h" in the drawings, and a tapered probe 16, designated "p" in the drawings. The preferred embodiment of the shaft has an overall length of slightly less than six inches and the probe covers about one quarter of this length. The preferred diameter of the handle is approximately 0.100 inches and the distal extremity 18 of the probe has a diameter of approximately 0.035 inches. While the foregoing configuration is preferred in order to provide an instrument that is properly balanced for ease of use, a handle size that is easy to hold and will not inadvertently break or unnecessarily bend, a considerable amount of dimensional variation is acceptable.

The above described general shape permits injection molding of a one-pieced shaft from a particular material that provides the necessary combination of ductility, stiffness and tip size. As described above and can be seen in FIG. 2 of the drawings, the prior art achieves this combination with a two-piece configuration that is far more costly to manufacture. In addition, by injection molding the shaft, a break line 20 can be formed as part of the molding process rather than having to cut the line as a separate step in the manufacturing process.

The preferred material for the shaft is fiberglass filled nylon. In order to provide sufficient ductility that the shaft will not break in use and still be stiff enough to prevent it from being bent during its intended use, the fiberglass must constitute 5 to 20 percent of the volume of the shaft. Ideally, the fiberglass would constitute 10 percent of the shaft.

After the shaft is constructed, a fiber tip can be applied to its end in the conventional manner to complete the swab.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A swab for collecting cell samples from the urethra of a human penis comprising:

(a) an elongate unitary shaft having a handle at one end and a probe at the other end;

(b) said handle having a constant diameter, circular cross-section;

(c) said probe having a circular cross-section which tapers toward the distal extremity thereof;

(d) a fiber tip located at the distal extremity of said probe; wherein (e) said shaft is nylon filled 5 to 20 percent by volume with fiberglass.

2. The swab of claim 1 wherein said shaft is nylon filled 10 percent by volume with fiberglass.

3. The swab of claim 1 wherein said probe covers approximately 25 percent of the overall length of said shaft.

4. The swab of claim 1 wherein said probe has a constant taper with the diameter of the distal extremity being approximately one third of the diameter of the handle.

5. The swab of claim 1 wherein the diameter of said handle is approximately 0.100 inch and the diameter of the distal extremity of said probe is approximately 0.035 inch.

6. The swab of claim 1 wherein said tip covers approximately one half of the length of said probe.

7. The swab of claim 1 wherein said shaft is formed by injection molding and a score line is formed in said handle as a part of the molding process proximate the midpoint of said shaft.

* * * * *